(12) United States Patent
Cox

(10) Patent No.: US 8,466,265 B2
(45) Date of Patent: Jun. 18, 2013

(54) THERAPEUTIC ANTIBODY PURIFICATION METHOD AND METHOD OF USE

(75) Inventor: John Cox, Victoria (AU)

(73) Assignee: CSL Limited, Parkville, Victoria (AU)

( * ) Notice: Subject to any disclaimer, the term of this patent is extended or adjusted under 35 U.S.C. 154(b) by 306 days.

(21) Appl. No.: 12/681,050

(22) PCT Filed: Oct. 2, 2008

(86) PCT No.: PCT/AU2008/001466
§ 371 (c)(1),
(2), (4) Date: Jul. 6, 2010

(87) PCT Pub. No.: WO2009/043103
PCT Pub. Date: Apr. 9, 2009

(65) Prior Publication Data
US 2010/0266596 A1    Oct. 21, 2010

Related U.S. Application Data

(60) Provisional application No. 60/976,896, filed on Oct. 2, 2007.

(51) Int. Cl.
*C07K 1/16* (2006.01)
*C07K 1/30* (2006.01)
*C07K 1/34* (2006.01)

(52) U.S. Cl.
USPC ............ 530/413; 530/417; 530/418; 530/422

(58) Field of Classification Search
None
See application file for complete search history.

(56) References Cited

U.S. PATENT DOCUMENTS

| | | | | |
|---|---|---|---|---|
| 5,750,349 A * | 5/1998 | Suzuki et al. | ............. | 435/7.1 |
| 6,743,427 B1 * | 6/2004 | Schenk | ............. | 424/130.1 |
| 7,834,144 B2 * | 11/2010 | Peretz et al. | ............. | 530/328 |
| 2002/0009445 A1 | 1/2002 | Du et al. | | |
| 2005/0165222 A1 * | 7/2005 | Leete et al. | ............. | 530/387.1 |
| 2006/0099211 A1 | 5/2006 | Monthe et al. | | |

OTHER PUBLICATIONS

Chandra S et al. (1999) Virus reduction in the preparation of intravenous immune globulin: in vitro experiments. Transfusion, 39(3):249-257.*
Pierce Biotechnology Technical Resource, "Optimize elution conditions for immunoaffinity purification." Published Nov. 2004.*
International Search Report issued on Nov. 19, 2008 in application No. PCT/AU2008/001466.
Du et al., "Human anti-β-amyloid antibodies block β-amyloid fibril formation and prevent β-amyloid-induced neurotoxicity," Brain, vol. 126, pp. 1935-1939, 2003.
Li et al., "Overcoming antigen masking of anti-amyloidbeta antibodies reveals breaking of B cell tolerance by virus-like particles in amyloidbeta immunized amyloid precursor protein transgenic mice," BMC Neuroscience, vol. 5, pp. 1-7, Jun. 8, 2004.
Li et al., "Improvement of a low pH antigen-antibody dissociation procedure for ELISA measurement of circulating anti-Aβ antibodies," BMC Neuroscience, vol. 8, pp. 1-11, Mar. 20, 2007.
Chung et al., "Dissociation of low density lipoprotein-antibody precipitates at alkaline pH," Journal of Lipid Research, vol. 8, pp. 631-635, 1967.
Necula et al., "Small Molecule Inhibitors of Aggregation Indicate that Amyloid β Oligomerization and Fibrillization Pathways are Independent and Distinct," Journal of Biological Chemistry, vol. 282, No. 14, pp. 10311-10324, 2007.

* cited by examiner

*Primary Examiner* — Elizabeth C Kemmerer
*Assistant Examiner* — Kimberly A Ballard
(74) *Attorney, Agent, or Firm* — Foley & Lardner LLP

(57) ABSTRACT

A method of preparing anti-b amyloid immunoglobulin involves treating human plasma anti-b amyloid immunoglobulin under alkaline conditions, such as at pH 10.25 to 11.75 using diethylamine HCl, to dissociate b amyloid protein therefrom. Typically, the anti-b amyloid immunoglobulin is present in human immunoglobulin preparations obtained from plasma or serum. Anti-b amyloid immunoglobulin prepared by the method is substantially free of b amyloid protein and has therapeutic activity in compositions and/or methods for treating a disease or condition associated with b amyloid plaques, such as Alzheimer's disease.

14 Claims, 2 Drawing Sheets

THERAPEUTIC ANTIBODY PURIFICATION METHOD AND METHOD OF USE

TECHNICAL FIELD

THIS INVENTION relates to preparation of immunoglobulin. More particularly, this invention relates to preparation of an anti-β amyloid immunoglobulin which may be suitable for immunotherapy of Alzheimer's disease.

BACKGROUND

Alzheimer's disease is a neurodegenerative disease that, in its most common form, is found in people over age 65. Approximately 15 million people worldwide have Alzheimer's disease.

Clinical signs of Alzheimer's disease are characterized by progressive cognitive deterioration, together with declining activities associated with daily living and by neuropsychiatric symptoms or behavioral changes.

Alzheimer's disease is characterized by the accumulation of plaque in brain tissues that is composed of β amyloid peptides. Administration of anti-β amyloid-antibodies to a mouse model of Alzheimer's disease appears to reduce β amyloid deposits in the mouse brain and restore or increase cognitive function or at least the rate of cognitive decline.

Naturally-occurring antibodies against β amyloid peptides are present in human serum. Administration of human immunoglobulin preparations obtained from human serum into humans is associated with a decrease in β amyloid-peptide levels in the cerebrospinal fluid. [US2002/0009445.] Recent clinical trial data shows beneficial outcomes in both behaviour and cognition in Alzheimer's disease patients treated with intravenous immunoglobulin ("IVIg") (www.news-medical.net/?id=40383).

However, such IVIg preparations contain significant amounts of neurotoxic β amyloid peptides and exhibit significant variation in antibody affinity and titre.

SUMMARY

Preparations of anti-β amyloid immunoglobulin are provided under alkaline conditions where β amyloid protein is sparingly soluble and hence less able to re-bind anti-β amyloid immunoglobulin.

In one aspect, a method of preparing an anti-β amyloid immunoglobulin involves treating an initial anti-β amyloid immunoglobulin under alkaline conditions sufficient to dissociate β amyloid protein, or a fragment thereof, from said initial anti-β amyloid immunoglobulin.

Suitably, the anti-β amyloid immunoglobulin prepared according to the method is substantially free of bound β amyloid protein.

In another aspect, a method of preparing a composition involves preparing an anti-β amyloid immunoglobulin by treating an initial anti-β amyloid immunoglobulin under alkaline conditions sufficient to dissociate β amyloid protein, or a fragment thereof, from said initial anti-β amyloid immunoglobulin; and combining the anti-β amyloid immunoglobulin with an acceptable carrier, diluent or excipient.

In yet another aspect, an isolated or purified anti-β amyloid immunoglobulin is provided, prepared by treating an initial anti-β amyloid immunoglobulin under alkaline conditions sufficient to dissociate β amyloid protein, or a fragment thereof, from said initial anti-β amyloid immunoglobulin.

In still yet another aspect, a composition comprises an anti-β amyloid immunoglobulin, prepared by treating an initial anti-β amyloid immunoglobulin under alkaline conditions to dissociate β amyloid protein, or a fragment thereof, from said initial anti-β amyloid immunoglobulin; and an acceptable carrier, diluent or excipient.

In one embodiment, the composition is suitable for treating a disease or condition associated with β amyloid plaques, such as Alzheimer's disease.

In a further aspect, a method of treating a disease or condition associated with β amyloid plaques in a mammal involves administering to said mammal an anti-β amyloid immunoglobulin prepared by treating an initial anti-β amyloid immunoglobulin under alkaline conditions to dissociate β amyloid protein, or a fragment thereof, from said initial anti-β amyloid immunoglobulin, to thereby treat said disease or condition in said mammal.

In one embodiment, the disease or condition associated with β amyloid plaques is Alzheimer's disease.

Other objects, features and advantages will become apparent from the following detailed description. The detailed description and specific examples are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples where it will be obviously useful to those skilled in the prior art.

Throughout this specification, unless the context requires otherwise, the words "comprise", "comprises" and "comprising" will be understood to imply the inclusion of a stated integer or group of integers but not the exclusion of any other integer or group of integers.

DETAILED DESCRIPTION

Figure 1:
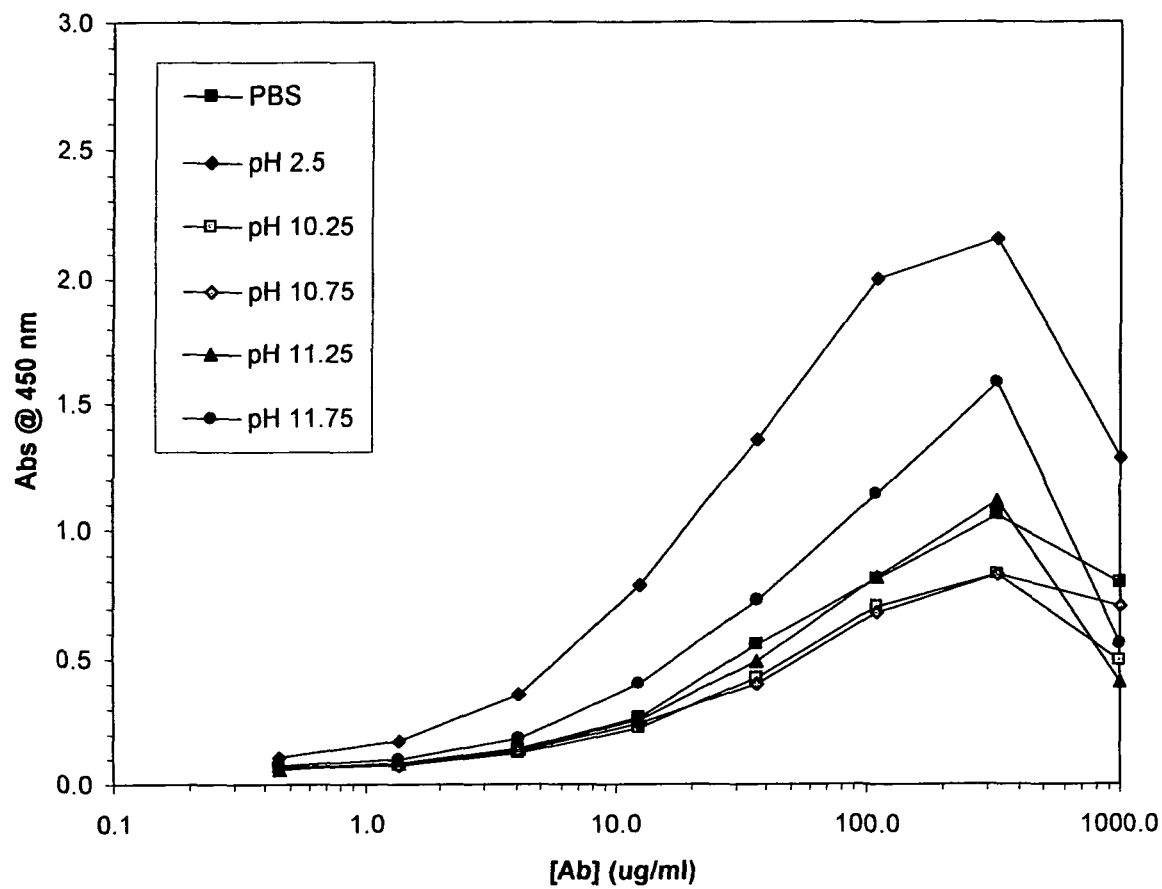
FIG. 1: ELISA comparing anti-β amyloid immunoglobulin preparation in the presence of (A) glycine buffers: glycine HCl pH 2.5; glycine NaOH pH 10.25; glycine NaOH pH 10.75; glycine NaOH pH 11.25; and glycine NaOH pH 11.75.

Specifically-bound β amyloid protein can be removed from preparations of anti-β amyloid immunoglobulins under alkaline conditions. Purification of IVIg anti-β amyloid immunoglobulin under acid conditions (e.g. about pH 2) results in soluble β amyloid protein, which can rebind to anti-β amyloid immunoglobulin, particularly when back-neutralisation commences.

Alkaline treatment of anti-β amyloid immunoglobulin, even at a pH as low as about pH 10.5, dissociates β amyloid protein from the anti-β amyloid immunoglobulin, under which conditions the β amyloid protein remains substantially insoluble and unable to be rebound by the anti-β amyloid immunoglobulin. The method is particularly suited to large scale and/or industrial preparation of anti-β amyloid immunoglobulin from human IVIg.

The improved efficiency of anti-β amyloid immunoglobulin after treatment under alkaline conditions on an industrial scale provides a more commercially viable process for producing anti-β amyloid immunoglobulin.

In one aspect, a method of preparing anti-β amyloid immunoglobulin involves treating an initial anti-β amyloid immunoglobulin under alkaline conditions sufficient to dissociate immunoglobulin-bound β amyloid protein, or a fragment thereof, from said initial anti-β amyloid immunoglobulin.

In another aspect, there is provided isolated or purified anti-β amyloid immunoglobulin prepared by the method as hereinbefore described.

By "isolated" is meant present in an environment removed from a natural state or otherwise subjected to human manipulation. Isolated material may be substantially or essentially free from components that normally accompany it in its natural state, or may be manipulated so as to be in an artificial state together with components that normally accompany it in its natural state.

By "purified" is meant enriched, concentrated or otherwise having a specific activity, amount or concentration greater than in an initial state or form.

Isolated or purified anti-β amyloid immunoglobulin may be substantially free off β amyloid protein.

By "substantially free" is meant that at least 50%, at least 60%, at least 65%, at least 70%, at least 75%, at least 80%, at least 85%, at least 90% or at least 95-99%, of the anti-β amyloid immunoglobulin molecules are not bound to, or bound by, β amyloid protein or fragments thereof.

As used herein a "protein" is an amino acid polymer which may be a peptide or a polypeptide. Generally, the term "peptide" as used herein is a protein having no more than sixty (60) contiguous amino acids.

The term "β amyloid protein" includes within its scope amyloid precursor protein (APP) and fragments thereof, including but not limited to the peptide fragments described in United States Publication 2006/0099211, for example.

It will be appreciated that as used herein, the term "immunoglobulin" includes any antigen-binding protein product of the human immunoglobulin gene complex, including human immunoglobulin isotypes IgA, IgD, IgM, IgG and IgE and antigen-binding fragments thereof. Examples of antigen-binding fragments include, but are not limited to, Fab, F(ab)$_2$, Fv, scFv, etc.

Preferably, the anti-β amyloid immunoglobulin prepared as hereinbefore described is, or comprises, IgG.

A preferred source of initial or starting anti-β amyloid immunoglobulin is human serum or plasma. Immunoglobulin preparations obtained from this source are typically administered by various routes including intramuscular, intravenous and subcutaneous and are thus often referred to as "IMIg", "IVIg", "SCIg" or similar. One particular non-limiting example of a source for use in the method is plasma, or a plasma fraction obtained by the Cohn fractionation process, such as Cohn Supernatant I (fibrinogen depleted plasma) or solubilised and clarified Fraction II+III.

The initial anti-β amyloid immunoglobulin, such as in the form of IVIg, can be delipidated and/or depleted of euglobulin by methods well understood in the art, such as described hereinafter in the Examples.

The initial anti-β amyloid immunoglobulin can be subjected to at least one anion exchange chromatographic step prior to alkaline treatment. In certain embodiments, first and second sequential anion exchange chromatographic steps may be used. In other embodiments a combination of anion and cation exchange chromatography steps may be used.

To achieve an alkaline pH for dissociation of β amyloid protein from anti-β amyloid immunglobulin, any suitable alkali may be used, typically in the form of a buffer solution. Such alkaline buffers are well known in the art and may be readily selected by a person of skill in the art.

By way of example only, alkaline buffers may include carbonate buffers, borate buffers, tri-sodium hydrogen phosphate buffer, diethylamine HCl, triethylamine HCl, glycine NaOH, 2-amino-2-methyl-1,3-propanediol (AMPD), N-tris (hydroxymethyl)methyl-4-am-inobutanesulphonic acid (TABS), 3-[(1,1-dimethyl-2-hydroxyethyl)amino]-hydroxypropanesulphonic acid (AMPSO), 2-(N-cyclohexylamino) ethanesulphonic acid (CHES), 3-(cyclohexylamino)-2-hydroxy-1-propanesulphonic acid (CAPSO), 2-amino-2-methyl-1-propanol (AMP), 3-cyclohexylamino-1-propanesulphonic acid (CAPS) and 4-(cyclohexylamino)-1-butanesulphonic acid (CABS).

A preferred alkaline buffer is diethylamine HCl.

Preferred alkaline conditions include a pH in the range 8.5-11.75.

More preferably, the pH is in the range 10.75-11.75.

Advantageously, the pH is in the range 11.25-11.75.

Elution at alkaline pH (e.g. about pH 11 or above) yields insoluble aggregates of β amyloid protein which cannot rebind anti-β amyloid immunoglobulin. The pH then can be neutralized to a lower pH (e.g. to about pH 9) without forming soluble β amyloid protein. Insoluble β amyloid protein can be removed at that pH before further neutralizing to an appropriate formulation pH, typically in the range pH 4.0-7.4. A non-limiting example is about pH 4.8 for IVIg preparations. It will be appreciated that lower pH conditions such as pH 4.8 are typically used for IVIg preparations, as the lower pH helps to minimise dimer/aggregate formation. It is however noted that IMIg formulations (where higher dimer/aggregate levels can be tolerated) may be at a closer to neutral pH (e.g. about pH 6.5).

Removal of β amyloid protein may then be performed by any method known in the art. Non-limiting examples of such methods include filtration such as nanofiltration and chromatography such as for example hydrophobic interaction chromatography. Alternatively, β amyloid aggregates can be removed by centrifugation, such as continuous flow centrifugation. It will also be appreciated that soluble forms of β amyloid protein may also be removed, for example, by diafiltration using a suitable molecular weight cut-off membrane, of about 10 to 30 kDa cutoff.

In one non-limiting embodiment, a method of preparing an anti-β amyloid immunoglobulin, comprises:
 (i) treating an initial anti-β amyloid immunoglobulin with a diethylamine HCl buffer at a pH in the range 10.75-11.75 to thereby substantially dissociate bound β amyloid protein from said anti-β amyloid immunoglobulin;
 (ii) partially neutralizing the pH at (i) to about pH 9;
 (iii) removing β amyloid protein;
 (iv) neutralizing the pH at (ii) to a pH in the range about pH 4.0-7.4; and
 (v) collecting anti-β amyloid immunoglobulin.

In one further embodiment, the anti-β amyloid immunoglobulin preparation is subjected to viral inactivation. Preferably, viral inactivation removes both enveloped and non-enveloped viruses. In one non-limiting embodiment, size exclusion may be used to remove viruses as small as approximately 20 nanometers.

In some embodiments, the β amyloid precipitate is subjected to the virus filtration step under conditions that enable removal of both virus and the β amyloid protein or fragments thereof.

Anti-β amyloid immunoglobulins prepared as hereinbefore described may be particularly efficacious in compositions and/or methods for treatment of Alzheimer's disease and other diseases or conditions associated with β amyloid plaques.

Thus, in one aspect, a method of treating a disease or condition associated with β amyloid plaques in a mammal involves administering to said mammal an anti-β amyloid immunoglobulin prepared by treating an initial anti-β amyloid immunoglobulin under alkaline conditions to dissociate β amyloid protein, or a fragment thereof, from said initial anti-β amyloid immunoglobulin.

In another aspect, a method of preparing a composition involves preparing an anti-β amyloid immunoglobulin involves treating an initial anti-β amyloid immunoglobulin under alkaline conditions sufficient to dissociate β amyloid protein, or a fragment thereof, from said initial anti-β amyloid immunoglobulin; and combining the anti-β amyloid immunoglobulin with an acceptable carrier, diluent or excipient.

In yet another aspect, a composition comprises an anti-β amyloid immunoglobulin, prepared by treating an initial anti-β amyloid immunoglobulin under alkaline conditions to dissociate β amyloid protein, or a fragment thereof, from said initial anti-β amyloid immunoglobulin; and an acceptable carrier, diluent or excipient.

Carriers, diluents and excipients may be pharmaceutically, veterinarily and/or immunologically acceptable, as is well understood in the art.

In general terms, by "carrier, diluent or excipient" is meant a solid or liquid filler, binder, diluent, encapsulating substance, coating or lubricant that may be safely administered to an animal, preferably a human. Depending upon the particular route of administration, a variety of acceptable carriers diluents or excipients, well known in the art may be used, as for example described in Remington's Pharmaceutical Sciences (Mack Publishing Co. N.J. USA, 1991).

By way of example only, these may be selected from a group including sugars, starches, cellulose and its derivatives, malt, gelatine, talc, calcium sulfate, vegetable oils, synthetic oils, lower alcohols, polyols, alginic acid, phosphate buffered solutions, emulsifiers, wetting agents, lubricants such as sodium or magnesium stearate, isotonic saline and pyrogen-free water.

The anti-β amyloid immunoglobulin preparations have enhanced therapeutic efficacy and/or reduced risk of β amyloid protein toxicity upon administration to patients with Alzheimer's disease.

In one non-limiting embodiment, the anti-β amyloid immunoglobulin preparations of the invention can be administered intravenously or subcutaneously to patients to prevent or treat Alzheimer's disease.

The anti-β amyloid immunoglobulin preparations can be administered in a single dose or in a dose repeated once or several times over a certain period. The appropriate dosage varies according to various parameters. Such parameters include the physiological status of the individual treated, the immunoglobulin preparation, the mode and frequency of administration, and the like.

Dosages of anti-β amyloid immunoglobulin preparations can vary depending upon the age, weight and physiological status of the patient. By way of example only, immunologlobulin prepared according to the invention may be administered once a week or once every two weeks or once every four, five, six or more weeks. The amount of immunoglobulin administered can vary and may depend upon the purity, affinity and avidity of the immunoglobulin preparation.

By way of example only, the amount may be about 0.001 g to about 10 g per kg body weight; about 0.01 g to about 5 g per kg body weight; about 0.1 g to about 3 g per kg body weight; about 0.5 g to about 2 g per kg body weight or about 0.8 to about 1.5 g per kg body weight of anti-13 amyloid immunoglobulin administered to a patient per dose.

A non-limiting example of a clinically effective human dosage regime is about 0.2 g/kg once every two weeks or 0.8 g/kg once every four weeks.

Besides Alzheimer's disease in humans, the immunoglobulin preparations can be used in a variety of veterinary applications relevant to immunotherapy of non-human mammals such as livestock, domestic pets, performance animals and the like.

EXAMPLES

Large Scale Preparation of IVIg Treated to Remove Bound β Amyloid

Anti-β amyloid immunoglobulin preparation can be manufactured according to the process described below.

Particularly preferred starting materials for use in the method of the present invention are plasma, or plasma fractions obtained by the Cohn fractionation process, such as Cohn Supernatant I (fibrinogen depleted plasma) or solubilised and clarified Fraction II+III.

Frozen plasma typically 1,250 kg to 10,000 kg plasma/plasma equivalents (6,250-50,000 whole blood donations) is softened at a temperature of −5° C. immediately prior to being thawed over a period of 12 to 24 hours. The thawed plasma forms a cryoprecipitate and an immunoglobulin containing cryosupernatant. The cryosupernatant is typically separated from the cryoprecipitate by continuous flow centrifugation wherein the effluent temperature does not exceed 5° C.

The cryosupernatant solution may then be diluted to 4-6% w/v and sufficient cold ethanol (95% v/v) added at neutral pH to achieve an ethanol concentration of 8% v/v prior to being incubated at −2° C. in order to precipitate fibrinogen (Fraction I). The Fraction I can be removed from the immunoglobulin containing supernatant (Supernatant I) by centrifugation and/or filtration.

In alternate embodiments the Supernatant I may be exposed to higher concentrations of ethanol in order to precipitate the immunoglobulin component as Fraction II+III. The Fraction II+III can then be resolubulised and clarified by filtration in order to prepare a starting material.

Where the starting material is plasma or other immunoglobulin-containing material containing lipoproteins, such as Supernatant I, the lipoproteins are preferably removed from the starting material by adsorption or precipitation under appropriate conditions to avoid or minimise the loss of immunoglobulin. A particularly preferred adsorbent material for use in accordance with the present invention is a finely divided silicon dioxide (silica) adsorbent such as Aerosil, for example having a particle size in the range of from 5-50 nm.

Supernatant I is mixed with a filter aid such as Diacel 150 at 2-8° C. prior to Aerosil being added. The mixture is stirred until the Diacel and Aerosil are dispersed prior to being filtered using a filter press device. The retained volume in the filter press device may be recovered by flushing using 0.5 M NaCl.

The conductivity of the Delipidated Supernatant I is reduced in order to prepare the solution for anion exchange chromatography. This may be achieved using an ultrafiltration membrane with a nominal cut off of not less than 10,000 daltons. After this, the pH is adjusted to pH 5.2 in order to precipitate euglobulin-like proteins. The euglobulin containing precipitate is removed by adding a filter aid such as Diacel to the mixture prior to being filtered using a filter press device. The retained volume in the filter press device may be recovered by flushing using 0.5 M NaCl.

The delipidated and euglobulin depleted material prepared as described above is fractionated by anion-exchange chromatography to produce a first immunoglobulin-containing fraction; and purification of the first immunoglobulin-containing fraction by a second anion-exchange chromatographic step provides a purified immunoglobulin containing solution.

Preferably, the delipidated material is diafiltered, pH adjusted and euglobulin depleted prior to fractionation by anion-exchange chromatography using DEAE-Sepharose FF under conditions of loading, pH and ionic strength which maximise the purity of immunoglobulin (crude IgG) obtained at this step. Preferably, fractionation of the delipidated, euglobulin-depleted material is effected on a DEAE-Sepharose FF column at pH 5.2 and at a conductivity of 0.5-1.0 mS/cm. In particular, these conditions ensure the maximal separation of transferrin from immunoglobulins even though the physico-chemical properties of transferrin closely approximate those of immunoglobulins. Generation of a relatively pure immunoglobulin preparation at this step facilitates the subsequent use of a second anion-exchange step to generate pure final product under pH conditions that ensure the loading capacity of the resin is adequate for a practical commercial process and that sub-class recovery is appropriate.

The second anion-exchange chromatographic step comprises purification of the immunoglobulin-containing fraction with macro-porous anion-exchange resins under conditions of loading, ionic strength and pH which generate a highly purified product with intact sub-class distribution, low IgA and IgM concentration and anti-A and anti-B levels within accepted pharmacopoeidial limits. Specifically, the use of macro-porous resins with a pore size of greater than 100 nm (such as Macro-Prep HQ, MacroPrep Q, Poros HQ, Q Hyper DM) can be used at pH of 6.0-6.6 and conductivity 0.7-1.5 mS/cm, to provide adequate adsorptive capacity to remove contaminating proteins to provide a Pure immunoglobulin G (Pure IgG) containing preparation.

In other embodiments, where the starting material is resolubilised Fraction II+III or other immunoglobulin-containing material which is already lipoprotein-depleted and partially purified, the material is simply subjected to final purification by passage through the column of macro-porous anion-exchange resin as described above.

The pure IgG solution is then concentrated by ultrafiltration to about 2% w/v and an appropriate buffering agent added (such as glycine-NaOH, ethanolamine-HCl or di-sodium hydrogen phosphate). The β amyloid is dissociated from the anti-β amyloid immunoglobulin contained within the pure IgG solution by adjusting the pH to 11.75 using 0.2 M diethylamine HCl over a period of about 2 hours in the presence of continuous mixing at 2-8° C. The pH adjusted pure IgG is incubated with mixing for at least 30 minutes at pH 11.75. The pH then can be neutralized to a lower pH (e.g. to about pH 9) without forming soluble β amyloid protein.

The insoluble precipitate containing β amyloid is removed from the pure IgG by loading the solution onto a hydrophobic interaction chromatography (HIC) column (such as Toyopearl 650C, Sepharose Fast Flow HIC, Source HIC or Macro-Prep HIC) at less than 40 g of protein per L of resin. The column is pre-equilibrated in an appropriate buffer, such as phosphate buffer, in the presence of 1.5 M NaCl at a pH of around 9.0. The IgG is subsequently eluted from the HIC column using a 60 minute linear gradient from 1.5 M to 0 M NaCl at a flow rate of 60-200 cm/hr. The eluted protein is then pH adjusted to 4.8 using 0.1 M hydrochloric acid or 0.1 M sodium hydroxide and stored at 2-8° C. prior to further processing.

In an alternate embodiment the insoluble precipitate containing β amyloid is removed from the pure IgG by loading the solution onto a hydrophobic charge induction chromatography (HCIC) column (such as MEP Hypercel) at less than 20 g of protein per L of resin. The column is pre-equilibrated in an appropriate buffer, such as phosphate or Tris buffer at a neutral or basic pH. The IgG is subsequently eluted using 20 mM sodium acetate buffer at pH 4.8. The eluted IgG containing preparation can be stored at 2-8° C. prior to further processing.

In an alternate embodiment, the insoluble precipitate containing β amyloid is removed from the pure IgG by addition of a filter aid (such as Diacel) and optionally 2 M NaCl and HIC resin (such as Toyopearl 650C, Sepharose Fast Flow HIC, Source HIC or MacroPrep HIC). The HIC resin is added at less than 40 mg of resin per L of protein. The mixture is stirred at 2-8° C. for at least 30 minutes prior to being clarified by centrifugation and/or filtration. The clarified solution is then pH adjusted to 4.8 using 0.1 M hydrochloric acid or 0.1 M sodium hydroxide and stored at 2-8° C. prior to further processing.

In yet another embodiment the insoluble precipitate containing β amyloid is removed from the pure IgG by loading the solution onto a size exclusion column containing a resin such as Sephacryl S400HR. The immunoglobulin fraction is eluted from the column using a buffer such as 50 mM sodium acetate, pH 4.8 at 10-50 cm/hr. The pH of the eluted protein is then adjusted to 4.8 using 0.1 M hydrochloric acid or 0.1 M sodium hydroxide and stored at 2-8° C. prior to further processing.

In a further embodiment, the insoluble precipitate containing β amyloid is removed from the pure IgG by continuous flow centrifugation.

Preferably, the anti-β amyloid immunoglobulin preparation is subjected to viral inactivation, for example by two dedicated virus clearance steps: pH 4 incubation at 37° C. for 10 hours to inactivate enveloped viruses and virus filtration to remove, by size exclusion, both enveloped and non-enveloped viruses as small as approximately 20 nanometers.

In some embodiments, pure IgG containing β amyloid precipitate is subjected to the virus filtration step under conditions that enable removal of both virus and the β amyloid.

The viral inactivated anti-β amyloid immunoglobulin preparation is then pH adjusted to pH 4.8 using 0.1 M sodium hydroxide and 0.1 M hydrochloric acid and concentrated to approximately 12% w/v by ultrafiltration using a membrane of nominal cut off of at least 30,000 daltons. The solution is diafiltered against at least 6 volumes of water while maintaining the pH at 4.8 by the addition of 0.1 M hydrochloric acid or 0.1 M sodium hydroxide. Final formulation is achieved by adding approximately 250 mmol/L of L-proline as a stabilizer and diluting to yield a concentration of 10% w/v in the final product. Following passage through clarifying filters the formulated bulk immunoglobulin is passed through a previously sterilised autoclaved sterilising membrane cartridge having a pore size of 0.22 μm or less into a vessel where it may be stored at 2-8° C. prior to dispensing. The product is aseptically dispensed into sterile 1 mL, 5 mL, 10 mL & 50 mL vials.

ELISA Analysis of IVIg pH Treatment 96-well Nunc MaxiSorb plates (Thermo Fisher Scientific, NY) were coated with Amyloid β-Protein Fragment 1-40 amide (SIGMA, MO), herein referred to as Aβ1-40, at 1 μg/ml in phosphate buffered saline (PBS), with 50 μl per well, overnight at 4° C. Unbound antigen was removed by washing wells with 350 µl 0.05% Tween-20 (Sigma, Mo.), PBS (TPBS). Antigen coated and blank uncoated plates were blocked with 2% bovine serum albumin (BSA) (Sigma, Mo.), PBS, with 50 µl per well, for 2 hours at room-temperature. Unbound BSA was removed by washing wells with 350 µl TPBS.

IntragamP (CSL Limited, Parkville, Australia), herein referred to as IVIg, was diluted to 20 mg/ml in PBS and then diluted 1/5 in 0.2 M glycine (Sigma, Mo.) at pH 2.5, 10.25, 10.75, 11.25 and 11.75; or 0.2 M diethylamine (Sigma, Mo.) at pH 10.25, 10.75, 11.25 and 11.75. After 20 minutes incubation at room temperature pH treated IVIg was neutralized with an equal volume 2.0 M Tris-HCl pH 8.0 (Sigma, Mo.) and then diluted 1/2 into 1% BSA, TPBS. IVIg was 3-fold serial diluted in 1% BSA, TPBS in a 96-well Nunc V-bottom plate (Thermo Fisher Scientific, NY) and 100 µl transferred to the BSA blocked plates. Plates were incubated for 1 hour at room-temperature before unbound IVIg was removed by washing wells twice with 350 µl TPBS.

Secondary antibody Anti-Human IgG (gamma chains) affinity isolated HRP conjugate raised in sheep (Millipore, Mass.) diluted 1/2000 in 1% BSA, TPBS was transferred, 50 µl per well, and incubated for 20 minutes at room-temperature. Unbound secondary antibody was removed by washing wells twice with 350 µl TPBS. Assay was developed with TMB/E Solution (Millipore, Mass.), 50 µl per well, incubated at room-temperature for 10 minutes for colour to develop and stopped with 2.0 M phosphoric acid, 25 µl per well. Developed plate was scanned at an absorbance of 450 nm, 0.1 seconds in a Wallac Victor 2 (Perkin Elmer, Mass.) plate reader. Results are shown in FIG. 1 and FIG. 2.

Figure 2:
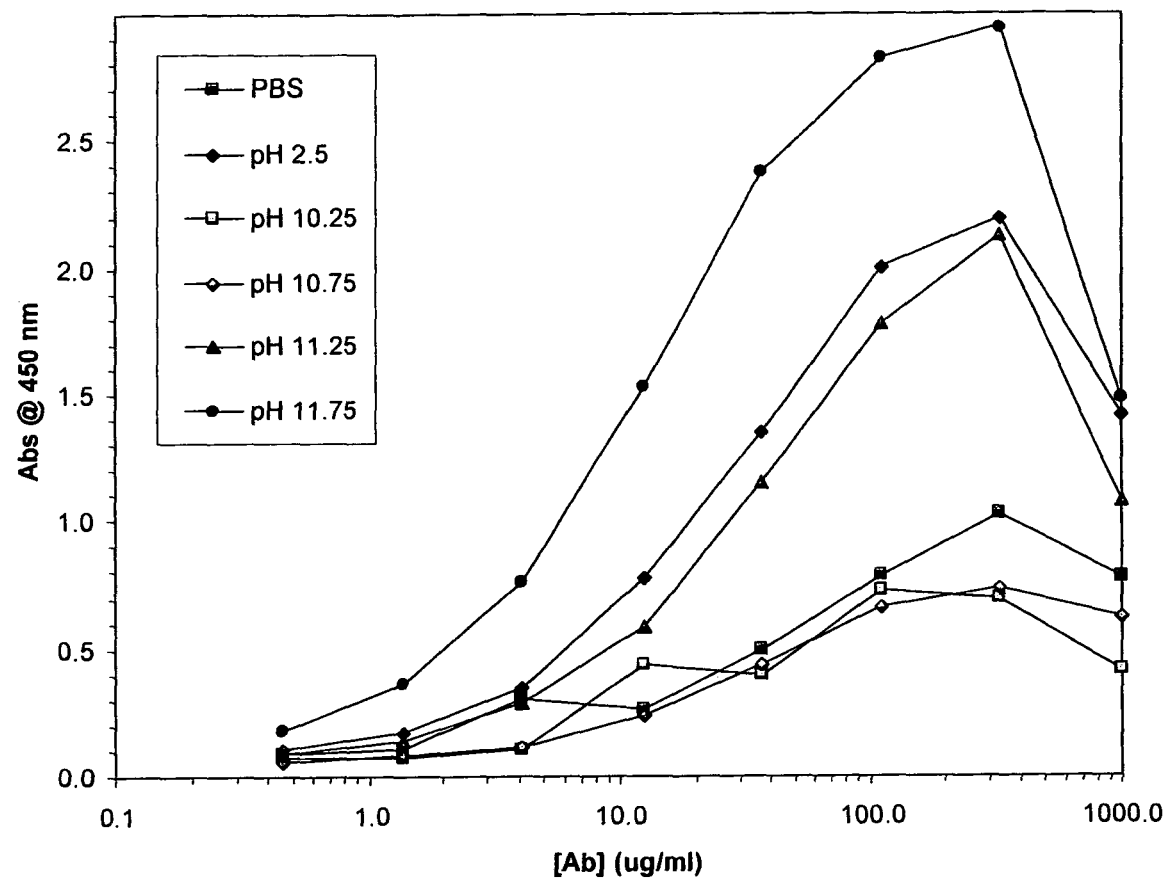
FIG. 2: ELISA comparing anti-β amyloid immunoglobulin preparation in the presence of diethylamine HCl buffers: pH 10.25; pH 10.75; pH 11.25; and pH 11.75 with a glycine HCl pH 2.5 control.

Referring to FIG. 1 and FIG. 2, both glycine NaOH and diethylamine HCl alkaline buffers dissociated anti-β amyloid IgG from the initial IVIg samples. Diethylamine HCl was superior to glycine NaOH, particularly at a pH above 11.25. These data also demonstrated that diethylamine HCl alkaline buffers at a pH above 11.25 (particularly at pH 11.75), were superior to glycine HCl pH 2.5 buffer in dissociating anti-β amyloid IgG from the initial IVIg samples.

Accordingly, it is proposed that alkaline buffers are suitable for dissociating anti-β amyloid immunoglobulins from β amyloid protein.

Of particular note is that diethylamine HCl alkaline buffers at a pH in the range pH 11.25-11.75, performed better than the glycine HCl pH 2.5 acid buffer tested in these experiments.

It will be appreciated that with respect to ranges as hereinbefore described (e.g. pH, dosages etc) any stated value in a range described herein may be used as a lower or upper value to construct another range, as appropriate.

Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

The invention claimed is:

1. A method of preparing anti-β amyloid immunoglobulin, comprising:
   (i) treating an anti-β amyloid immunoglobulin obtained from human serum or plasma under alkaline conditions at a pH of 11.25 to 11.75, sufficient to dissociate β amyloid protein, or a fragment thereof, from said anti-β amyloid immunoglobulin,
   (ii) at least partly neutralizing to about pH 9 without forming soluble β amyloid protein; and
   (iii) removing insoluble β amyloid protein.

2. The method of claim 1, wherein the removal of insoluble β amyloid protein is performed by filtration, chromatography or centrifugation.

3. The method of claim 1, further including (iv) neutralizing to about pH 4.8.

4. The method of claim 1, wherein the anti-β amyloid immunoglobulin prepared by the method is substantially free of β amyloid protein.

5. The method of claim 1, wherein the anti-β amyloid immunoglobulin has therapeutic activity with respect to a disease or condition associated with amyloid plaques.

6. The method of claim 1, further including a virus inactivation step.

7. The method of claim 1, further including (iv) neutralizing to a pH in the range 4.0 to about 6.5.

8. A method of preparing an anti-β amyloid immunoglobulin, comprising:
   (i) treating an initial anti-β amyloid immunoglobulin with a diethylamine HCl buffer at a pH in the range of 11.25-11.75 to thereby substantially dissociate bound β amyloid protein from said anti-β amyloid immunoglobulin;
   (ii) partially neutralizing the pH resulting at step (i) to about pH 9;
   (iii) removing β amyloid protein;
   (iv) neutralizing the pH resulting at step (ii) to a pH in a range about pH 4.0-7.4; and
   (v) collecting anti-β amyloid immunoglobulin.

9. A method of preparing an anti-β amyloid immunoglobulin pharmaceutical composition, comprising:
   (i) treating an anti-β amyloid immunoglobulin obtained from human serum or plasma under alkaline conditions at a pH in the range of 11.25 to 11.75, sufficient to dissociate β amyloid protein, or a fragment thereof, from said anti-β amyloid immunoglobulin;
   (ii) at least partly neutralizing to about pH 9 without forming soluble β amyloid protein; and
   (iii) combining the anti-β amyloid immunoglobulin with a pharmaceutically acceptable carrier, diluent or excipient.

10. The method of claim 9, wherein the composition comprises an amount of anti-β amyloid immunoglobulin effective for treating a disease or condition associated with β amyloid plaques in a mammal.

11. The method of claim 10, wherein the mammal is a human.

12. The method of claim 11, wherein the disease or condition is Alzheimer's disease.

13. The method of claim 9, further including (iv) neutralizing to a pH in the range 4.0 to about 6.5.

14. The method of claim 13, further including (iv) neutralizing to about pH 4.8.

* * * * *